United States Patent [19]

Russ et al.

[11] 4,383,875
[45] May 17, 1983

[54] METHOD FOR MAKING COSMETIC PENCILS

[75] Inventors: Julio G. Russ, Germantown; Donna L. Barrom, Arlington, both of Tenn.

[73] Assignee: Plough, Inc., Memphis, Tenn.

[21] Appl. No.: 296,386

[22] Filed: Aug. 26, 1981

[51] Int. Cl.³ .................... B65B 7/28; A61K 7/025; A61K 7/032

[52] U.S. Cl. .................... 156/69; 156/154; 156/187; 156/192; 156/264; 401/88; 401/98; 424/63; 424/64; 424/DIG. 5; 53/440; 29/415

[58] Field of Search ............ 156/69, 153, 154, 187, 156/192, 250, 264; 106/224, 230, 19, 245, 268; 132/88.7; 401/49, 88, 98; 53/440; 29/411, 415; 424/DIG. 5, 63, 64

[56] References Cited

U.S. PATENT DOCUMENTS 3,088,876  5/1963  Buth .................... 424/64
3,211,618 10/1965  Kambersky ............ 424/365

FOREIGN PATENT DOCUMENTS 2027343  2/1980  United Kingdom ....... 401/88

Primary Examiner—Edward C. Kimlin
Assistant Examiner—F. K. Wine
Attorney, Agent, or Firm—Warrick E. Lee, Jr.; Vincent H. Gifford; Bruce M. Eisen

[57] ABSTRACT

A method for making a cosmetic pencil having a lead of solvent-based cosmetic composition.

The leads are packaged in an airtight container, such as a plastic bag and stored in a freezer at temperature no higher than 0° for 12 to 168 hours. The leads are then stored at room temperature for at least two hours and unpackaged. Then the leads are encased in grooved slates to form an assembly which is wrapped with airtight wrapping.

8 Claims, 4 Drawing Figures

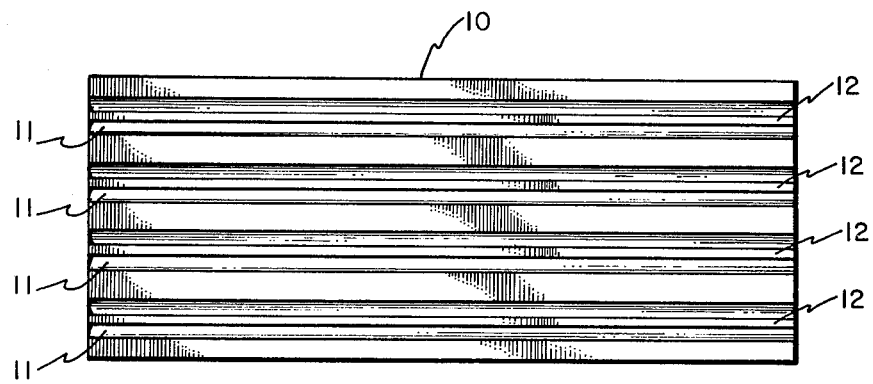
FIG. 2
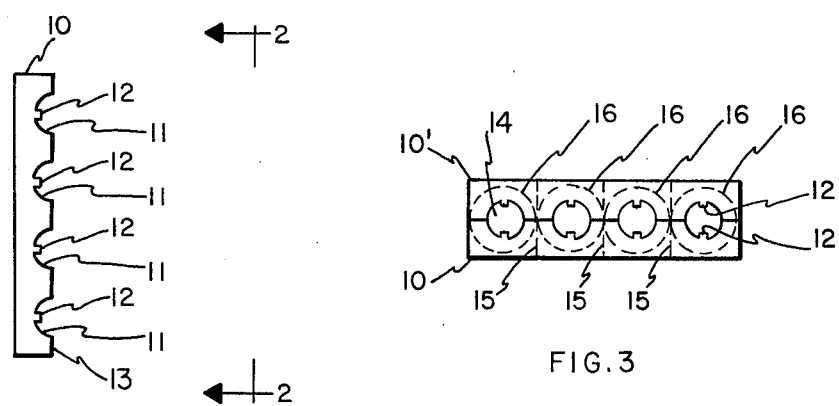
FIG. 1
FIG. 3
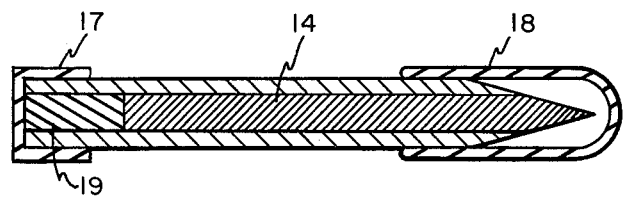
FIG. 4

METHOD FOR MAKING COSMETIC PENCILS

This invention relates to cosmetic pencils, such as eye shadow, eye liner, lipstick, and the like. More particularly this invention relates to cosmetic pencils wherein the cosmetic composition is solvent-based.

Prior-art methods for forming cosmetic pencils, merely enclose a cosmetic lead in wooden slats, without special pretreatment. These prior-art methods are not satisfactory for solvent-based systems, because the leads tend to be weak and the solvent evaporates, rendering the finished product unacceptable.

The present invention, which overcomes these problems, comprises a method for forming a cosmetic pencil having a lead of solvent-based cosmetic composition comprising at least one wax or resin solvent for the wax or resin, and pigment comprising the steps of:

(a) packaging said lead in an airtight container and storing the packaged lead in surroundings having temperature no higher than 0° C. for 12 to 168 hours, thereafter
(b) storing the packaged lead in room-temperature surroundings for at least 2 hours, thereafter
(c) removing said lead for said airtight container,
(d) providing a pair of slats having grooved surfaces, said grooves upon joining of said surfaces forming a channel having inside dimension slightly larger than an outside dimension of said lead,
(e) forming an assembly by inserting said lead into a groove and attaching said grooved surfaces to each other by adhesive bonding such that said lead is in said channel, and thereafter
(f) wrapping said assembly with airtight wrapping such that said wrapping covers at least a portion of the outer surface of said assembly.

The term "solvent-based cosmetic composition" is intended to mean a cosmetic composition containing at least one wax or resin and a solvent for the wax or resin. Solvent-based cosmetic compositions are disclosed in U.S. Pat. Nos. 3,088,876 (May 1963, Buth) and 3,211,618 (October 1965, Kambersky). Another composition for use with the present method contains:

9 percent Candelilla wax;
15 percent $C_{18-36}$ acid triglyceride;
4 percent microcrystalline wax;
25 percent petroleum distillate;
18.2 percent cosmetically acceptable oil;
0.5 percent preservatives and antioxidants, and;
28.3 percent pigments.

The term "lead" is intended to mean the pencil's core made of cosmetic composition.

BRIEF DESCRIPTION OF THE DRAWING

FIG. 1 is an end view of a slat having a plurality of grooves.

FIG. 2 is a view of the slat of FIG. 1 along the lines 2—2.

FIG. 3 is an end view of two slats attached at matching surfaces.

FIG. 4 is a longitudinal sectional view of a finished pencil made in accordance with the invention.

DETAILED DESCRIPTION OF THE INVENTION

A solid lead made of a solvent-based cosmetic composition by techniques well known in the art is provided. Preferably the lead will be cylindrically shaped having round or elliptical cross section with diameter of 1/10" to ½", more preferably about ¼".

The lead must be packaged in an airtight container and stored in surroundings having temperatures no higher than 0° C. for 12 to 168 hours. The preferable storage temperature and time are 0° C. to −15° C. for 12 to 24 hours. This step may be accomplished by layering a plurality of leads in a single box lined by a 2 mil thick low density polyethylene bag and sealing the bag. The box containing the sealed bag is then placed in a freezer at the appropriate temperature for the appropriate time.

The packaged lead is then removed from the freezer and allowed to stand at room temperature (i.e. from about 20° to 28° C.) for at least 2 hours.

The lead is then removed from the airtight container in preparation for the next step. The unpackaged lead must not be allowed to stand in the open too long, or at least part of the solvent will evaporate.

A pair of slats, preferably wooden, having grooved surfaces is provided. The matching surfaces, when joined must form a channel having inside dimension slightly larger than the outside dimension of the lead.

It is preferable to provide slats having a plurality of matching grooves as illustrated in FIGS. 1 and 2. Slat 10 has longitudinal grooves 11 in the top surface shown in FIG. 2. Preferably each grove has a longitudinal ridge 12 about 0.01" deep to help hold the lead tightly during prolonged storage and use. The grooves (excluding the ridges) have inside dimension slightly larger than the outside dimension of the lead. For example if the leads are circular having radius of 0.125", the radius of the groove may be from 0.003" to 0.010" larger than 0.125". A second slat 10' (see FIG. 3), preferably identical to slat 10, is provided. The two slats have identically spaced grooves, i.e., have matching grooves.

An assembly as in FIG. 3 is formed by attaching the matching surfaces to each other such that a lead is in each channel. For the slats illustrated in FIG. 3, this can be done by lightly coating at least one matching surface, such as the top surface and grooves of slat 10 with glue, such as a water dispersion of ethylene-vinyl acetate copolymer. Leads 14 are then placed in grooves 11 and second slat 10' is attached, forming the assembly of FIG. 3. A wooden plug 19 (see FIG. 4) may be placed in one end of the grooves. The slats are held together until the glue dries; preferably for at least 4 hours.

To form cylinder-shaped assemblies, each of which contains a single lead, the slats are rounded along lines 16 (see FIG. 3) and then cut into single-lead assemblies along line 15.

Preferably no more than 24 hours after the single-lead assemblies have been framed, they are wrapped with airtight wrapping such that the wrapping covers at least a part of the outer surface of the assembly. This is preferably accomplished by coating the lateral surface of the assemblies with clear varnish, allowing the varnish to dry and wrapping the coated surface with 1.5 mil thick metallized Mylar. The Mylar may be adhered to the pencils by pressure sensitive adhesive. The Mylar may be preprinted with the manufacturer's trademark, the cosmetic type and color, etc.

One end of the wrapped pencils may then be capped with an airtight cap, element 17 of FIG. 4.

If it is desirable to point the pencils, they are stored in a cooler at 5° C. to −15° C., preferably 0° C. to −5° C. for 2 to 20 hours. The pencils are then removed from the freezer and pointed while they are still cold. After pointing, the pencils are fitted with and airtight metal point protector, element 18 of FIG. 4.

The completed pencils may now be stored at room temperature for prolonged periods without deterioration of the cosmetic composition.

The method of the present invention has the following advantages over prior-art systems:
1. There is very little solvent evaporation.
2. The leads are stronger, i.e., have a better structure.

What is claimed is:

1. A method for forming a cosmetic pencil having a lead of solvent-based cosmetic composition comprising at least one wax or resin, solvent for the wax or resin, and pigment comprising the steps of:
   (a) packaging said lead in an airtight container and storing the packaged lead in surroundings having temperature no higher than 0° C. for 12 to 168 hours, thereafter
   (b) storing the package lead in room-temperature surroudings for at least two hours, thereafter
   (c) removing said lead from said airtight container,
   (d) providing a pair of slats having grooved surfaces, said grooves upon joining of said surfaces forming a channel having inside dimension slightly larger than an outside dimension of said lead,
   (e) forming an assembly by inserting said lead into a groove, and attaching said grooved surfaces to each other by adhesive bonding such that said lead is in said channel, and thereafter
   (f) wrapping said assembly with airtight wrapping such that said wrapping covers at least a portion of the outer surface of said assembly.

2. The method of claim 1 wherein said assembly is cylindrically shaped having first and second ends and wherein said airtight wrapping covers the lateral area of said cylinder, further comprising capping said first end of said cylinder with an airtight cap.

3. The method of claim 1 wherein said slat's grooved surfaces contain a plurality of matching grooves further comprising:
   forming a plurality of cylindrically-shaped assemblies, each of which has a first end and a second end and contains a single lead, after said step (e) attachment;
   capping said first end with an airtight cap,
   and wherein said step (f) wrapping covers the lateral area of said cylinders.

4. The method of claim 3 further comprising the steps of storing said wrapped cylinders in surroundings having temperature from 5° to −15° C. for 2 to 20 hours, thereafter pointing said second ends, and fitting airtight point protectors over said points.

5. The method of claim 4 wherein said lead are cylindrical having diameter of 1/10 to ½ inches.

6. The method of claim 5 wherein said solvent based composition comprises candelilla wax, $C_{18-36}$ acid triglyceride, microcystalline wax, petroleum distillate and cosmetically acceptable oil.

7. The method of claim 5 wherein said step (a) storage takes place at temperature of 0° to −15° C. for 12 to 24 hours.

8. A pencil made by the method of claims 1, 2, 3, 4, 5, 6, or 7.

* * * * *